US00PP20006P2

(12) United States Plant Patent
Hamernik

(10) Patent No.: US PP20,006 P2
(45) Date of Patent: May 19, 2009

(54) *WEIGELA* PLANT NAMED 'APRIL SNOW'

(50) Latin Name: *Weigela*
Varietal Denomination: April Snow

(76) Inventor: Harlan Hamernik, 519 Bryan St., Clarkson, NE (US) 68629

( * ) Notice: Subject to any disclaimer, the term of this patent is extended or adjusted under 35 U.S.C. 154(b) by 0 days.

(21) Appl. No.: 12/070,667

(22) Filed: Feb. 19, 2008

Related U.S. Application Data

(60) Provisional application No. 60/903,620, filed on Feb. 26, 2007.

(51) Int. Cl.
*A01H 5/00* (2006.01)

(52) U.S. Cl. ..... Plt./226

(58) Field of Classification Search ..... Plt./226
See application file for complete search history.

*Primary Examiner*—June Hwu

(57) ABSTRACT

A new cultivar of *Weigela* plant named 'April Snow' that is characterized by its pure white flowers and bright green leaves. In combination, these traits set 'April Snow' apart from all other varieties of *Weigela* known to the inventor.

1 Drawing Sheet

Genus: *WEIGELA*.
Species: *praecox*.
Denomination: 'APRIL SNOW'.

BACKGROUND OF THE INVENTION

This application claims the benefit of priority under 35 U.S.C. 119(e) of U.S. Provisional application No. 60/903,620, filed on Feb. 26, 2007, entitled *WEIGELA* Plant named 'April Snow'.

The present invention relates to a new and distinct cultivar of *WEIGELA* grown as an ornamental plant for use in the garden and landscape. The new cultivar is known botanically as *WEIGELA praecox* and will be referred to hereinafter by the cultivar name 'APRIL SNOW'.

The new cultivar 'APRIL SNOW'was selected by the inventor from a crop of seed sown *Weigela praecox* (species, unpatented) at the inventor's nursery in Clarkson, Nebr. It was the only plant in a group of 2500 seedlings with pure white flowers instead of pink flowers as is typical of the species.

The closest comparison plant is the commonly sold *Weigela praecox*. 'APRIL SNOW' differs from the pink-flowered species in respect of its large pure white flowers.

Asexual reproduction by softwood cuttings of the new cultivar 'APRIL SNOW' was accomplished in 2000 in Clarkson, Nebr. by the inventor. Since that time, under careful observation, the unique characteristics of the new *Weigela* plant have been uniform, stable and reproduced true to type in successive generations of asexual reproduction.

SUMMARY OF THE INVENTION

The distinguishing characteristics of the new *Weigela* cultivar 'April Snow' are as follows. These traits in combination distinguish 'April Snow' as a new and distinct cultivar when compared with all other existing varieties of *Weigela* known to the inventor. 'April Snow' has not been tested under all possible conditions and phenotypic differences may be observed with variations in environmental, climatic, and cultural conditions, however, without any variance in genotype.

1. 'APRIL SNOW' bears pure white funnel-shaped flowers in dense clusters from April through June.

2. The flowers of 'APRIL SNOW' maintain their color with no tendency to turn pink with age.
3. The foliage of 'APRIL SNOW' is bright green.
4. 'APRIL SNOW' is vigorous and reaching a height of 6 feet in height and 5 feet in width.
5. 'APRIL SNOW' is suitable for use as a garden or landscape plant.
6. 'APRIL SNOW' grows well in moist well-drained soils in full sun to partial shade.
7. 'APRIL SNOW' is hardy to USDA Zone 4.

BRIEF DESCRIPTION OF THE DRAWING

The accompanying color drawing illustrates the distinguishing characteristic of 'APRIL SNOW', namely the cymes of pure white flowers. In all other respects, 'APRIL SNOW' resembles the parental species *Weigela praecox,* whose flowers are colored pink.

The plant used for preparing the drawing was grown outdoors at the inventor's nursery in Clarkson, Nebr.

Figure 1:
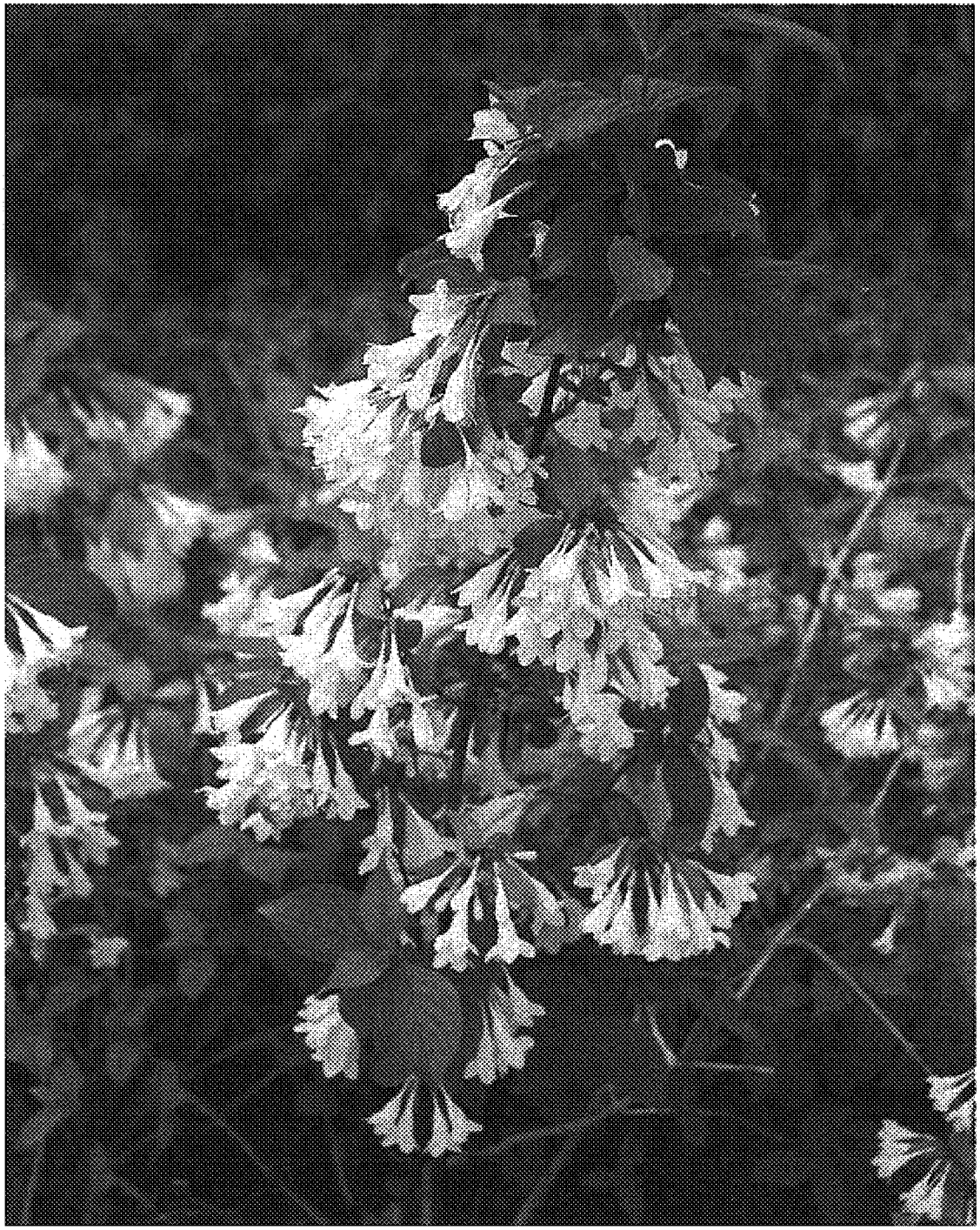

The drawing has been made using conventional techniques and although colors may appear different from actual colors due to light reflectance, they are as accurate as possible by conventional photography.

BOTANICAL DESCRIPTION OF THE PLANT

The following is a detailed description of the *Weigela* cultivar named 'April Snow'. Data was collected in Colfax, N.C. from 6 month old plants that were container grown outdoors. Color determinations were made in accordance with The 2001 Royal Horticultural Society Colour Chart from London England, except where general color terms of ordinary dictionary significance are used. The growing requirements are similar to the species and there are no disease problems known to the inventors.

Botanical classification: *Weigela praecox* 'April Snow'.
Genus: *Weigela*.
Species; *praecox*.
Use: In the landscape.

Parentage: 'April Snow' is a chance plant found in a crop of seed produced *Weigela praecox*.
Growth habit: Upright tending to spread as it matures shrub.
Suitable container sizes: 1–3 gallon containers.
Dimensions in first year: 45 cm in height and 60 cm in width.
Dimensions when mature: 1.8 m in height and 1.5 m in width.
Hardiness: USDA Zone 4.
Propagation: Stem cuttings.
Time to initiate roots: 5–6 weeks are required to produce roots on an initial cutting.
Crop time: One year to 18 months are required to produce a finished one-gallon container from a rooted cutting.
Root system: Fibrous.
Light: Plant in full sun or partial shade.
Soil: Plant in moist but well drained soil.
Type: Deciduous shrub.
Seasonal interest: White flowers in early spring.
Branching habit: Densely branching.
Stem:
*Twig color.*—144C.
*Stem color.*—176B.
*Twig shape.*—Terete, ridged.
*Stem shape.*—Terete, persistent decurrent ridges on opposite sides of stem.
*Twig width.*—2 mm to 3 mm.
*Stem width.*—3 mm to 4 mm.
*Stem length.*—85 mm to 120 mm.
*Internode length.*—20 mm to 30 mm.
*Stem surface.*—With scattered ciliate to strigose hairs, especially on decurrent ridges.
*Surface structures.*—White hairs, kinked, 1 mm to 2 mm in length.
Foliage:
*Leaf arrangement.*—Opposite.
*Leaf division.*—Simple.
*Leaf shape.*—Elliptic to obovate.
*Leaf dimensions.*—40 mm to 65 mm in length and 25 mm to 30 mm in width.
*Leaf apex.*—Narrowly acute to subacuminate.
*Leaf base.*—Cuneate to rounded.
*Leaf venation pattern.*—Pinnate, reticulate.
*Vein color* (*abaxial and adaxial*).—139D.
*Margin.*—Dentate to serrate, slightly mucronate on some teeth; undulate.
*Leaf surface* (*adaxial*).—Glabrous, except along midrib; hairs, when present, scattered, long strigose.
*Young leaf color* (*adaxial*).—138A.
*Young leaf color* (*adaxial*).—138B.
*Mature leaf color* (*adaxial*).—136B to 137A.
*Mature leaf color* (*abaxial*).—138A to 138B.
*Leaf attachment.*—Short petiolate.
*Petiole dimensions.*—2 mm to 4 mm in length and diameter.
*Petiole surface.*—With scattered, strigose hairs.
*Surface structures.*—White translucent hairs, 1 mm to 2 mm in length.
*Petiole color.*—139D.
Inflorescence:
*Inflorescence form.*—Cymose.
*Quantity of flowers per inflorescence.*—2 to 5.
*Time and duration of flowering.*—Beginning in early spring and lasting 2 to 3 weeks.
Flower:
*Flower aspect.*—Salverform.
*Diameter of flower* (*including calyx, corolla, petals*).—8 mm to 25 mm.
*Height or depth of flower.*—25 mm to 35 mm.
*Bud.*—Shape: Elliptoid and tubular. Color: 157A. Dimensions: 10 mm to 15 mm in length and 3 mm to 4 mm in width. Surface: Covered with short tomentose very short (less than 1 mm long) matted hairs that are translucent to whitish in color.
*Bracteoles.*—Location: Paired at the base of peduncle. Description: Long, strap-like. Dimensions: 8 mm to 10 mm in length and less than 0.5 mm in width.
*Peduncle.*—Dimensions: 10 mm in length and 1 mm in width. Shape: Terete. Color: 145A tinged with 59A. Surface: Highly scattered, very short hairs translucent to whitish in color.
*Calyx.*—Shape: Funnel-shaped. Dimensions: 7 mm to 8 mm in length and 3 mm to 4 mm in diameter. Color (inner and outer surfaces): 145A. Outer surface: Covered with scattered, strigose hairs. Inner surface: Covered with dense, tomentose hairs.
*Sepals.*—Number: 5. Fused or unfused: Fused. Color (inner and outer surfaces): 145A. Outer surface: Covered with scattered, strigose hairs. Inner surface: Covered with dense, tomentose hairs.
*Corolla.*—Shape: Salverform Dimensions: 30 mm to 35 mm in length and 10 mm to 25 mm in width. Surface: Glabrous. Tube color: 193A basally, 145D apically. Number of lobes: Five. Shape of lobes: Ovate to ovate-elliptic. Lobe color: 156D.
*Petals.*—Fused or unfused: Fused. Number: Five. Color (both surfaces): 156D. Surface texture: Glabrous.
Reproductive Organs:
*Number of stamens.*—Five.
*Fused or unfused at base.*—Fused.
*Dimensions.*—10 mm in length and less than 1 mm in width.
*Filament color.*—156D.
*Anther shape.*—Elliptoid.
*Anther dimensions.*—3 mm to 4 mm in length and 1 mm in width.
*Anther color.*—155A.
*Pollen color.*—Pale yellow-white.
*Pollen amount.*—Minimal.
*Number of pistils.*—1.
*Pistil shape.*—Filamentous.
*Pistil dimensions.*—25 mm to 30 mm in length and 0.5 mm to 1 mm in width.
*Pistil color.*—193A.
*Pistil surface.*—Glabrous.
*Stigma shape.*—Hemispherical.
*Stigma dimensions.*—Less than 1 mm in length and 1 mm to 2 mm in width.
*Stigma color.*—193A.
*Style shape.*—Filamentous.
*Style dimensions.*—25 mm to 30 mm in length and less than 1 mm in width.
*Style color.*—193A to 156D.
*Ovary position.*—Superior.
*Ovary shape.*—Ovoid.
*Ovary dimensions.*—Less than 1 mm in length and width.
*Ovary color.*—193A.
Fruit and seed: None observed to date.

What is claimed is:

1. A new and distinct variety of *Weigela* plant named 'April Snow' as described and illustrated.

* * * * *